(12) United States Patent
Swanson

(10) Patent No.: US 8,683,998 B2
(45) Date of Patent: Apr. 1, 2014

(54) MULTIPURPOSE CANNULA

(75) Inventor: Richard Swanson, Mukilteo, WA (US)

(73) Assignee: Koninklijke Philips N.V., Eindhoven (NL)

( * ) Notice: Subject to any disclaimer, the term of this patent is extended or adjusted under 35 U.S.C. 154(b) by 1523 days.

(21) Appl. No.: 11/969,690

(22) Filed: Jan. 4, 2008

(65) Prior Publication Data

US 2009/0173350 A1  Jul. 9, 2009

(51) Int. Cl.
*A61M 16/06* (2006.01)
*A61M 16/00* (2006.01)

(52) U.S. Cl.
USPC ............ 128/204.23; 128/207.18; 128/207.13; 128/204.21; 128/204.18; 128/200.26; 128/200.24

(58) Field of Classification Search
USPC ............. 128/200.24, 200.26, 203.22, 204.18, 128/204.21, 206.11, 207.13, 207.18, 128/207.14; 600/529, 537, 382, 386, 832
See application file for complete search history.

(56) References Cited

U.S. PATENT DOCUMENTS

| | | | |
|---|---|---|---|
| 4,602,644 A | 7/1986 | DiBenedetto et al. ......... 128/725 |
| 4,660,555 A * | 4/1987 | Payton ...................... 128/207.18 |
| 4,989,599 A | 2/1991 | Carter ...................... 128/207.18 |
| 5,046,491 A | 9/1991 | Derrick ..................... 128/200.24 |
| 5,099,836 A * | 3/1992 | Rowland et al. .......... 128/204.23 |
| 5,335,656 A | 8/1994 | Bowe et al. ............... 128/207.18 |
| 6,155,986 A * | 12/2000 | Brydon et al. ................ 600/538 |
| 6,439,234 B1 | 8/2002 | Curti et al. ................ 128/207.18 |
| 6,533,983 B2 | 3/2003 | Curti ............................. 264/219 |
| 6,655,385 B1 * | 12/2003 | Curti et al. ................ 128/207.18 |
| 6,799,575 B1 | 10/2004 | Carter ....................... 128/207.18 |
| 6,938,619 B1 | 9/2005 | Hickle ....................... 128/207.18 |
| 7,152,604 B2 * | 12/2006 | Hickle et al. ............. 128/207.14 |
| 7,305,988 B2 * | 12/2007 | Acker et al. .............. 128/204.18 |
| 7,462,154 B2 * | 12/2008 | Yamamori et al. ............ 600/532 |

* cited by examiner

Primary Examiner — Annette Dixon

(57) ABSTRACT

This invention relates to medical treatment and monitoring of a living body, and more particularly to a multipurpose apparatus and method for measuring a living body's respiratory airflow, analyzing the composition of a gas exhaled by a living body and/or insufflating a treating gas into the living body.

5 Claims, 3 Drawing Sheets

MULTIPURPOSE CANNULA

FIELD OF THE DISCLOSURE

This invention relates to medical treatment and monitoring of a living body, and more particularly to a multipurpose apparatus and method for measuring a living body's respiratory airflow, analyzing the composition of a gas exhaled by a living body and/or insufflating a treating gas into the living body.

BACKGROUND

When a living body, such as a human patient, is sick, being operated upon or undergoing sleep studies, it is often necessary to monitor air flow and in some cases to supplement the body's inhalation with a treating gas, such as oxygen or a gaseous anesthetic. In these instances, an accurate quantitative determination of the amount of at least one gaseous component, such as carbon dioxide, in the blood passing through the pulmonary alveoli of the living body is highly desirable. In addition, it is also desirable to have an accurate quantitative determination of the amount of air the patient is breathing. In intensive care situations or under a regional or general anesthetic, an accurate determination of the composition of the breathing gas in the pulmonary alveoli allows the bodily functions of a patient to be more readily supervised and treatment of the patient more favorably adapted to the state of those functions. Accurate measurements of at least one gaseous component in the exhalation of a living body also may help improve related diagnostic methods for determining bodily conditions. Measuring the concentration of at least one gaseous component in exhaled breathing gas may be conducted continuously to provide relatively short response times and to enable rapid alterations in an ongoing medical procedure, thereby preventing adverse effects or damage to the living body. One area of particular interest is the monitoring of end-tidal carbon dioxide, which is the partial pressure of the carbon dioxide component of exhaled gas at the end of exhalation in a spontaneously breathing patient. The quantitative monitoring of end-tidal carbon dioxide in spontaneously breathing patients who are unintubated (those not requiring intubation with an endotracheal tube) would be particularly useful for those unintubated patients who while awake are being treated with supplemental oxygen administration and are receiving regional or local anesthesia or are in a recovery room during emergence from residual general anesthesia.

Another area of concern is the use of cannulas on pediatric patients. The practice during pediatric sleep studies has been increasingly trending toward the measurement of end-tidal CO2 to ascertain the respiratory status of the pediatric patient. With the advent of nasal pressure monitoring for events of sleep apnea, the need for dual cannula capability has increased with pediatric patients that find two cannulas taped together cumbersome.

Yet another area of concern is accurately measuring the exhaled gases in a patient with a blocked nostril. Prior art such as a cannula which diverts gases from one nostril to one measuring device and gases from another nostril to another measuring device will provide inaccurate results if the patient has a single blocked nostril. U.S. Pat. No. 5,335,656 issued to Bowe, is a cannula with two nasal tubes. However this patent is directed to nasal tubes connected to a single narrow tube with a wall which partitions the hollow body.

U.S. Pat. No. 6,938,619 issued to Hickle is a mask free oxygen delivery and gas sampling system. However, the invention inserts two tubes in one nostril and no tubes in the patient's other nostril.

U.S. Pat. No. 4,989,599 issued to Carter is a cannula enclosed within another cannula. However, this patent does not have a hollow body to allow mixing of the gases from two nostrils.

U.S. Pat. No. 6,439,234 issued to Curti is a nasal cannula. However, the hollow body has a wall separating the hollow body into compartments.

U.S. Pat. No. 5,046,491 issued to Derrick is an apparatus to collect nasal and oral gases. However, the oral gas hood is used to collect oral gases and not as a mixing chamber to mix nasal and oral gases.

There is therefore a real need in the art for a multipurpose cannula that is small enough to be comfortable in a patient's nostrils yet be capable of measuring several variables and/or delivering a treating gas to a patient, even if the patient has a blocked nostril. One such example is that there is a need for an apparatus having the combined advantageous of insufflating a treating gas into the patient and sampling and analyzing a portion of the patient's exhaled breathing gas. Moreover, there is a real need in the art for simultaneously sampling and analyzing a portion of the patient's exhaled breathing gas and measuring the patient's airflow or simultaneously measuring a patient's airflow. Moreover, there is a real need for a cannula that would allow the accurate measurement of a patient's exhaled gases and insufflating a treating gas from patients with a blocked nostril.

SUMMARY OF THE DISCLOSURE

The invention is a cannula capable of multiple simultaneous uses. Specifically, the design of the hollow body of the cannula allows the measurement by at least two devices measuring multiple components from the gases exhaled from both the patients nostrils and mouth and/or insufflating a treating gas. In one example, the cannula disclosed herein allows simultaneous monitoring of the patient's respiratory airflow and delivery of a treating gas. In another example, the cannula allows simultaneous monitoring of patient respiratory airflow and sampling of exhaled gases for analysis. Additionally, the cannula could monitor a plurality of gas variables including carbon dioxide levels. These multiple uses are accomplished through the use of a hollow body which allows the mixing of the gases from the patient's nostrils and/or mouth to be connected and measured to multiple measuring devices. The use of the hollow body also provides more accurate measurements in certain situations.

The cannula's hollow body allows multiple uses because the hollow body could be connected to multiple measuring devices. Unlike the prior art, which concentrates on connecting only two devices per cannula, the invention's hollow body is capable of being connected to multiple devices. The hollow body provides the surface area to insert more than two tubes to enable the hollow body to be connected to more than two measuring devices. For example, this would allow the patient's respiratory airflow and gas composition measurements and administration of oxygen to be made simultaneously with the use of only one cannula when the hollow body is connected by three separate tubes to these devices.

The invention also provides more accurate results than the prior art because the hollow body of the invention is connected to at least two nasal and/or oral orifices of the patient. This allows simultaneous measurements of pressure and composition to be taken from the totality of gases exhaled by the patient instead of those gases exhaled by only one nostril. For example, if the patient has a blocked nostril, measurements from multiple orifices gives a more accurate reading of the gases exhaled by the patient compared to a cannula that only measures gases from one nostril. This is due to signal attenuation. This signal attenuation can be due to a blocked nostril or similar condition that causes an unequal flow of gases through each nostril of the patient. This is particularly a problem when the cannula being used has a separation inside the hollow body which allows measurement of exhaled gases only from one nostril. Specifically, a patient with a blocked left nostril will exhale significantly less gas through the blocked nostril than her other unblocked nostril. This will give an attenuated signal to the measuring device attached to the blocked left nostril.

This invention's accuracy over the prior art is due to the use of the hollow body. The hollow body captures the exhaled gases from both nostrils and/or the mouth. Thus, a single blocked nostril will not give a false reading as the totality of gases exhaled by the patient is captured by the hollow body from the other unblocked nostril and/or mouth. Additionally, the use of a hollow body as a common connection point to a plurality of measuring devices allows multiple signals to be recorded by all the measuring devices attached to the hollow body instead of only one device.

In addition, the invention measures pressures and simultaneously delivers treating gases better than the prior art. In the prior art such as two cannulas taped together, one nostril was used to obtain measurements and the other nostril was used to deliver oxygen to the patient. However, the administration of a given flow of oxygen through one nostril instead of two may have a greater drying effect on the single nostril to which oxygen is delivered. Thus, the amount of oxygen which can be successfully delivered for a long period of time through one nostril may be substantially less than that which could be delivered through two nostrils. For example, the administration of 3 liters per minute of oxygen through one nostril will have a drying effect on that nostril equivalent to the administration of 6 liters per minute through both nostrils. Thus, the quantity of oxygen that can be delivered to the patient is limited to the amount that can be fed through one nostril without undue crusting of nasal secretions and/or undue drying of nasal mucosa. In the current invention, the oxygen is delivered to both nostrils which would have less of a drying effect.

Additionally, this invention helps meet the need of sleep physiologic monitoring that uses two separate cannulas taped together at the patient's nose to sample exhaled gases or deliver a treating gas and/or to monitor a patient's respiratory airflow. Patients often find the use of two bulky cannulas placed in their nostrils cumbersome and sometimes this configuration even attenuates the signals of one, or both, of the individual cannulas attached to measuring devices. The use of this device enables only one set of nasal tubes to be inserted into the patient's nose o provide simultaneous pressure readings with gas analysis or therapeutic gas administration.

Thus, the invention allows the use of a single cannula for patient interface in order to make the patient more comfortable and provide a more accurate reading of the gases exhaled by the patient. The cannula of the present invention enables more accurate analyses and measurements of a patient's exhaled gas, minimizes patient discomfort, and enhances the delivery of treating gases.

BRIEF DESCRIPTION OF THE DRAWINGS

The objects and features of the present invention, which are believed to be novel, are set forth in the appended claims. The present invention, both as to its organization and manner of operation, together with further objects and advantages, may best be understood by reference to the following descriptions, taken in conjunction with the accompanying drawings, wherein:

DETAILED DESCRIPTION

Figure 1:
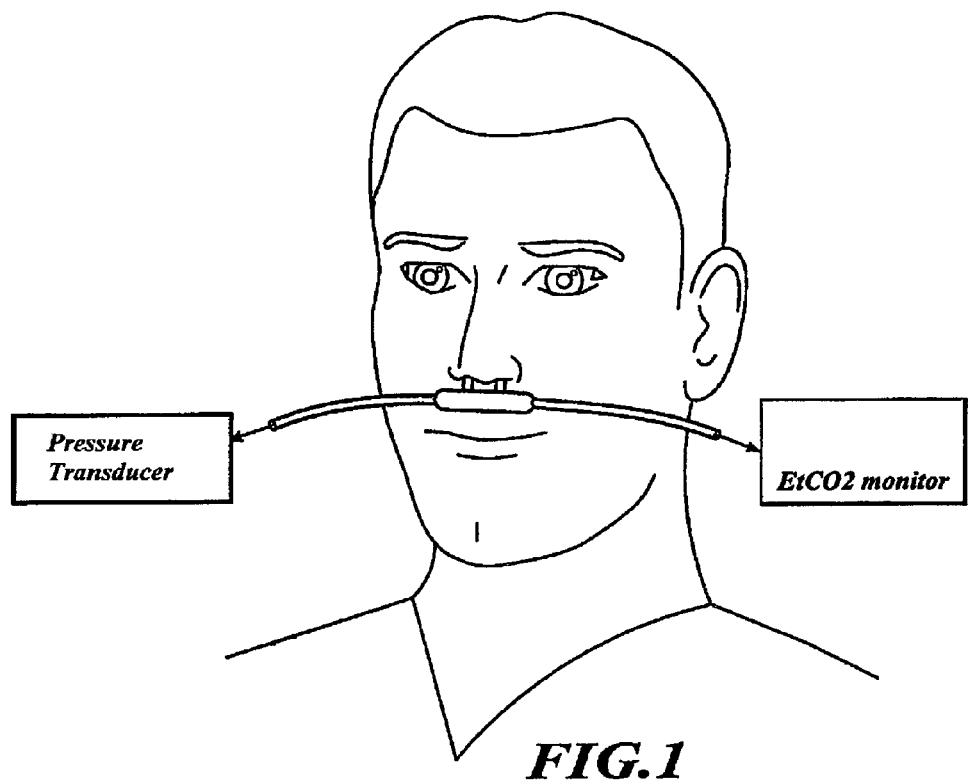
FIG. 1 is a plan view showing a patient's head with the invention's nostril tubes placed up her nose.
Figure 2:
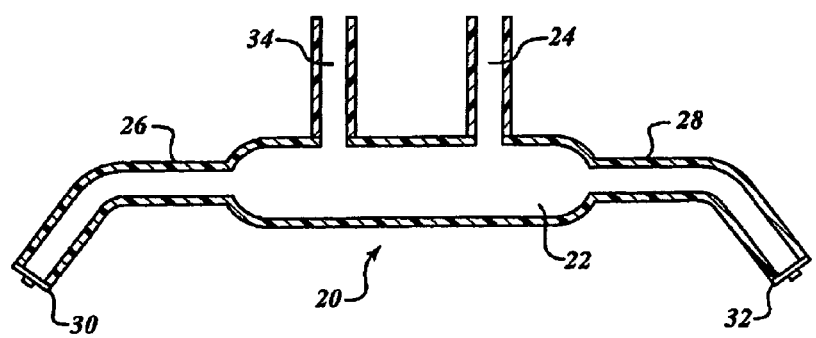
FIG. 2. is a cross sectional view along the center axis of an embodiment of the invention.

Referring to FIG. 2, there is shown a nasal cannula 20 having a hollow body 22 and a pair of nasal prongs 24 and 34, each adapted to fit within a corresponding nasal passage of the nose of a human patient as illustrated in FIG. 1.

Referring again to FIG. 2, hollow body 22 is also connected to connector tubes 26 and 28. These tubes are attached to connectors 30 and 32 respectively. Connectors 30 and 32 can be attached to any variety of measuring devices such as a pressure transducer and/or even to a treating gas. The tubes maybe obtained separately or supplied as part of the cannula, in which case one end of each of tubes 26 and 28 may be searlingly fixed in place by means such as adhesive composition or by fusion of the material of the septum to the material of the hollow body by solvent welding, sonic welding or the like creating an air-tight sealing engagement. The other ends of the tubing would then be connected to connectors 30 and 32.

The tubes 28 and 26 may be connected to a breathing gas analyzer or other systems for monitoring and measuring a patients exhaled gases. The nasal tubes 24 and 34 can withdraw a patients exhaled gases, through the hollow body, then through tubes 28 and 26 and to any connected measuring devices. A treating gas can also be delivered to the patient in a reverse fashion. Thus, the tubes, connectors, hollow body and nasal tubes all need to form a continuous gas tight apparatus. Additional tubes and connectors can be attached to hollow body 22 to connect other measuring devices and/or administer a treating gas. This would allow more than two devices to be attached to the invention simultaneously. Additionally, nasal tubes can also be tapered for easier insertion into the patient's nostrils.

The necessary sealing between tubes 26 and 28 and connectors 30 and 32 respectively may be accomplished by some form of adhesion, such as adhesive compounds, solvents or sonic welds. The connection between hollow body 22 and tubes 26 and 28 can be done in a similar fashion or the tubes and hollow body can be molded in one piece. Additionally, the connection between nasal tubes 34 and 24 and hollow body 22 can be done in a similar fashion or the nasal tubes and hollow body can be molded in a single piece. All seals in cannula 20 should be gas tight. Connections between the cannula 20 and the measuring devices and/or treating gas tank can be done by any method known to those of ordinary skill to create a gas tight seal.

The tubes 26 and 28 may have various shapes, angles and bend radii, which may suggest other geometries to those skilled in the art. The hollow body 22 may have various shapes, sizes, and forms, including manifolds and non-conventional cannula, which may suggest other geometries or designs to those skilled in the art.

In the embodiment shown in FIG. 1, the cannula 20 may have an elongated hollow body 22 which would be placed on the upper lip of the patient with nasal prongs 34 and 24 positioned within the corresponding nasal pages of the patient's nose. The position of hollow body 22 relative to the position and direction of the prongs 34 and 24 is such that the support provided by the hollow body 22 tends to keep the cannula 20 and its component parts in their correct position relative to the patient's nose and the nasal passages therein.

Hollow body 22 as well as cannula 20 as a whole is preferably constructed of plastic to prevent any gas leaks which allows the cannula to form a gas tight apparatus except for the nasal and/or oral tubes and the connectors 30 and 32. The inside of hollow body 22 serves to collect a small volume of gases the patient has exhales from both nostrils and/or mouth. The volume of air is then sampled by a measuring device such as a pressure transducer and/or a carbon dioxide monitor or any other appropriate gas measuring device. Hollow body 22 thus serves as a storage container for sampling of the patient's exhaled gases from a plurality of orifices. Additionally, if multiple treating gases are connected to cannula 20, hollow body 22 would serve to mix the treating gases so the patent could inhale them together instead of separately.

In one embodiment, hollow body 22 is provided in a variety of sizes and shapes to collect different volumes of air to facilitate different medical procedures which may be performed from a patient's nostrils or mouth.

Figure 3:
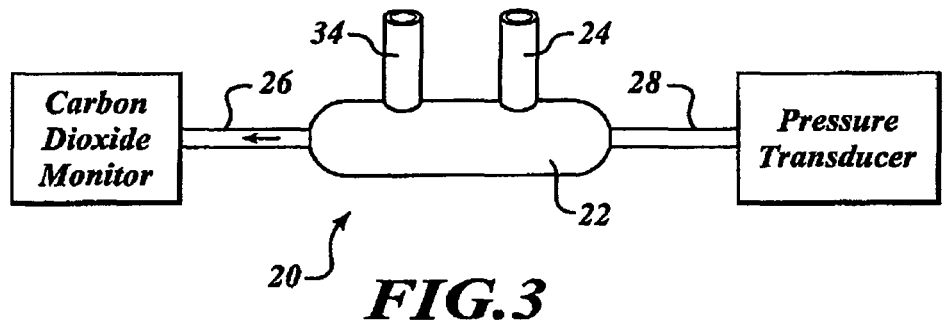
FIG. 3 is a plan view of the invention attached to a carbon dioxide monitor and a pressure transducer.
Figure 6:
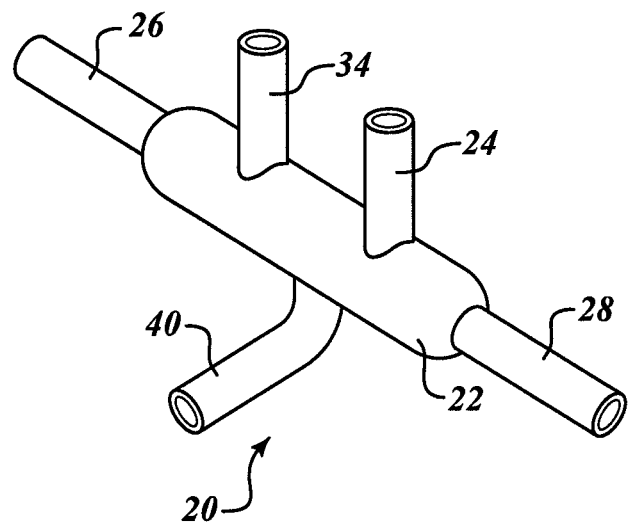
FIG. 6 is a plan view of the invention with an oral tube.
Figure 7:
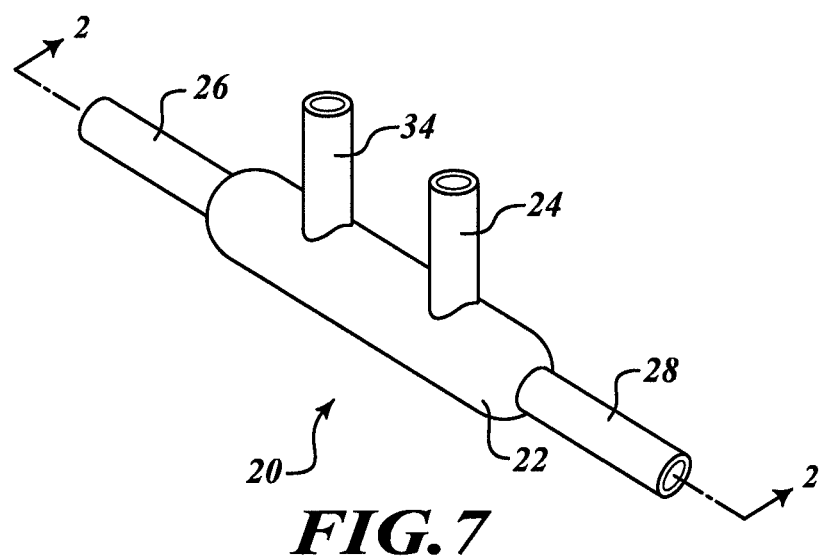
FIG. 7 is a plan view of the invention.

In another embodiment, such as in FIG. 3, cannula 20 is connected to a pressure transducer and a carbon dioxide monitor. In this embodiment, the patient would exhale gases into the cannula 20. The gases from both nostrils and/or mouth (if hollow body included an additional oral tube 40 as seen in FIG. 6) would mix in hollow body 22 and the gas would go to be aspirated by the carbon monoxide detector or any other suitable gas analysis device. The pressure transducer would detect the increase in pressure by the patient's exhaled gases and give a measurement of the patient's respiratory air flow. The blockage of a single nostril would not affect the reading of a single measurement device attached to cannula 20. This is because all measurements are taken from the totality of gases exhaled by the patient in hollow body 22 and not just one nostril like the prior art.

Figure 4:
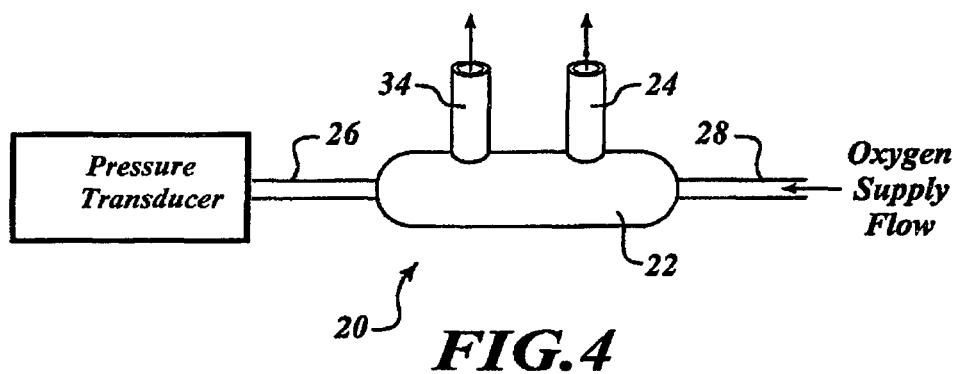
FIG. 4 is a plan view of the invention attached to a pressure transducer and oxygen supply.

In yet another embodiment as in FIG. 4, the cannula 20 would be attached to a pressure transducer and an oxygen supply. Here, the airflow from the oxygen supply would go from the oxygen source into one of the tubes, into hollow body 22 and out both nasal tubes. Here, the delivery of oxygen to the patient would not be hindered by a single blocked nostril because of the use of the hollow body. A measurement of the patient's respiratory airflow would also be measured from the pressure transducer. As the patient exhaled, the exhaled gases would enter hollow body 22 through one or both of the nasal tubes and the change in pressure, would be measured by the pressure transducer and would accurately predict the patient's respiratory airflow.

Figure 5:
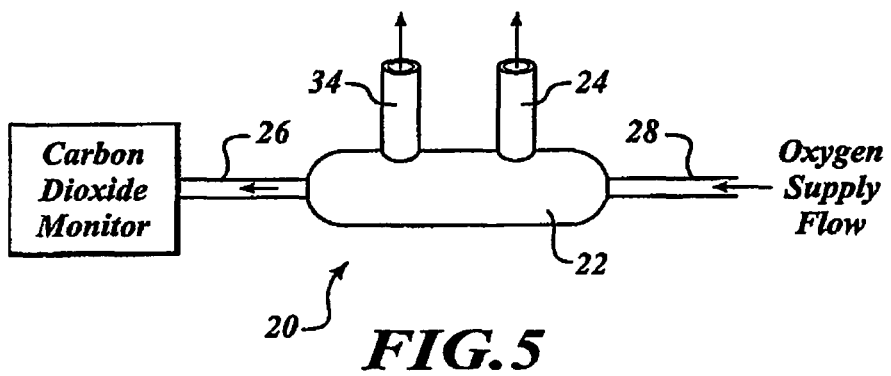
FIG. 5 is a plan view of the invention attached to an oxygen supply and a carbon dioxide monitor.

In another embodiment as in FIG. 5, the gas analyzer could be composed of a carbon dioxide analyzer while administering oxygen. In this example, the carbon dioxide analyzer would aspirate continuous samples which would reduce the pressure in the hollow body at a constant rate. As the patient's airflow changes, the resulting change in pressure would be in direct correlation to the patient's breathing. Even though the administration of oxygen would increase the pressure, this increase would be constant and the measurement of the patient's respiratory airflow would still be accurately measured. Thus, these constant pressure changes can be accounted for and an acute measurement of the patient's airflow can be calculated despite the pressure changes from any measuring devices extracting gas or the administration of a treating gas.

The preferred embodiment of the apparatus of this invention are preferred because such embodiments limit patient discomfort, are simply constructed and light weight, and cause minimal obstruction of the patient's facial surfaces and breathing passages. In addition, such preferred embodiments provide effective collection of respired gases, especially exhaled gases through nasal and/or oral tubes.

As shown and described herein, the preferred materials of construction used with the apparatus of this invention are light weight, flexible plastic tubing, sheeting and other stock materials. Nevertheless, it is within the concept of the method and apparatus of this invention that the elements of structure of the apparatus of this invention can be constructed from any material that is not harmful to, or causes discomfort to, the patient and that does not affect adversely the gas delivery, collection, sampling and analysis functions of the apparatus and method of this invention.

Experimental Measurements and Comparisons

In order to test the effectiveness of the cannula 20, actual measurements were made to show that the performance of the invention is substantially equivalent to cannulas previously cleared by the FDA for monitoring patient airflow and gas sampling and delivery.

EXAMPLES

The Invention vs. a Carbon Dioxide Gas Sampling Cannula and a Airflow Pressure Cannula Test Plan The cannula is designed to simultaneously monitor patient airflow and sample or deliver gas such as EtC02 or oxygen. To demonstrate this capability a side by side comparison with cannulas previously cleared by the FDA for airflow monitoring and carbon dioxide gas sampling and an oxygen cannula for gas delivery needs to be performed to show substantial equivalence of the devices.

Test Equipment—
  Pro-Tech PTAF2 (x2)
  Cadwell Sleep Easy EEGII PSG Data Acquisition Computer
  Smiths End Tidal CO2 (EtCO2) monitor (x2)
  Pro-Tech Pro-Flow Adult Nasal Cannula K-982293
  BCI/Smiths Sample Line, Nasal CO2, Adult K-822819
  Pro-Tech Pro-Flow MultiPurpose Cannula (The invention)
Comparison Tests:
Test 1—Compare the invention to Pro-Tech Pro-Flow Airflow Cannula described herein for equivalence of cannulas for pressure airflow signals.
Test 2—Compare the invention described herein to BCI/Smiths Sample Line, Nasal CO2, Adult for equivalence of cannulas as a gas sampling line.
Procedure Test 1
  The invention and Pro-Tech Pro-Flow Airflow Cannula were placed on a test subject at the same time. The Pro-Flow Airflow Cannula and the invention were each connected to separate PTAF sensors which were connected to the Cadwell Easy EEGII PSG Data Acquisition System for collection of the airflow signals. The invention gas line was connected to the Smiths EtCO2 Capnograph for analysis of the exhaled carbon dioxide. The test subject breathed normally for several minutes as data was collected. The airflow signals obtained with each cannula followed the same morphology with no significant differences.

Procedure Test 2

The invention and a BCI/Smiths Gas Sample Line Cannula were placed on a test subject at the same time. The BCI/Smiths Gas Sample Line Cannula and the invention were each connected to separate Smiths EtCO2 Capnographs and the invention's airflow line was connected to ProTech PTAF sensor which was connected to the Cadwell Easy EEGII PSG Data Acquisition System. Only one Capnograph could be connected at a time to the recording equipment.

The test subject breathed normally for several minutes as data was collected.

Samples of exhaled carbon dioxide gas analysis readings were obtained for test 2. The EtCO@ readings obtained were within 5%. The airflow signal was equivalent to that obtained in Test 1. The invention provided substantially equivalent signals compared to Pro-Tech Pro-Flow Airflow Cannula and the BCI/Smiths Sample Line, Nasal CO2, Adult cannula that comes standard with their Capnographs.

Test Three

The Invention Vs EtCO2 Gas Sampling & Gas Administering Cannula

The invention is designed to simultaneously monitor patient airflow and sample or deliver gas such as EtCO2 or oxygen. To demonstrate this capability a side by side comparison with cannulas previously cleared by the FDA for EtCO2 gas sampling and oxygen gas delivery needs to be performed to show substantial equivalence of the devices.

Test Equipment—
Pro-Tech PTAF2
Cadwell Easy EEG v1.7 PSG data acquisition computer
BCI/Smiths End Tidal CO2 (EtCO2) monitor
Salter Labs cannulae: 4002 Adult nasal CO2 sample cannula with oxygen delivery, both lines 7'K863883
4003 Adult dual oral/nasal CO2 sample cannula with oral form wire and oxygen delivery, both lines 7'K864902
4703 Pediatric divided cannula with 7' O2 line and 7' CO2 line
The cannula device described and claimed herein.

Testing—

Each cannula had two sets of connectors. In the models 4003 and 4002 these connectors actually go to two complete cannulas secured together which are placed onto the patient. Model 4703 has a septum in the "box" that the nasal prongs connect to, making two separate circuits. The invention cannula has two connectors that are essentially each at the end of a tube with the nasal prongs in the middle. Since each cannula has two connections they were each connected in to the pressure transducer and the carbon dioxide monitor so two waveforms for each cannula were recorded.

Each cannula gave viable waveforms for the monitoring of respiratory flow and EtCO2.

Model 4703, using one nasal prong for EtCO2 and one for pressure measurements was subject to the patency of the patient's nasal airways. When comparing the waveforms against itself it was observed that the test subject had better flow through one nare than the other. Models 4003 and 4002 (differing only in that 4003 has dual oral prongs and 4002 has no oral components) appeared to exhibit the best flow signals of all the cannulas tested. This is due to the fact that their dual nasal prongs fill the nares thereby increasing the pressure changes by causing a partial obstruction. These models were also difficult to fit to the test subject as the nasal prong "loops" were doubled in diameter and hard to fit behind subject's ears.

The invention described herein having just one tube for each nasal passage was the smallest, easiest to fit and tolerate of the cannulas. The signals for both the EtCO2 monitor and the pressure transducer were more than adequate for use during polysomnographical testing The dual cannulas piggybacked to monitor two different parameters are unwieldy in actual use. The split-chambered model using a single nasal prong for each monitor is hindered by the possibility that the patient may have nasal septum abnormalities negating one of the prongs effectiveness. The invention cannula is small and produces adequate signals for both monitors by the simple use of a single cannula with connections on each end and is substantially equivalent to the cannulas it was measured against.

Industrial Applicability

The disclosure herein has applicability to the field of medical devices and specifically to multipurpose cannula for exhaled gaseous pressure measurement, exhaled gas composition analysis and therapeutic gas administration through nasal and oral passageway.

In compliance with the statute, the invention has been described in language more or less specific as to structural features. It is to be understood, however, that the invention is not limited to the specific features shown or described, since the means and construction shown or described comprise preferred forms of putting the invention into effect. The invention is, therefore, claimed in any of its forms or modifications within the legitimate and valid scope of the appended claims, appropriately interpreted in accordance with the doctrine of equivalents.

What is claimed is:

1. An apparatus for measuring respiratory pressure from the nasal passageways of a patient and insufflating a treating gas into the nostrils of a patient, the apparatus comprising:
   a) a gas receiving hollow body;
   b) a pressure transducer for measuring pressure fluctuations in said hollow body;
   c) a treatment gas supply connected via a first conduit to said hollow body to provide a supply of treatment gas to the interior of said hollow body;
   d) a carbon dioxide monitor connected to said hollow body via a second conduit, for aspirating and receiving gases exhaled from the nostrils of a patient;
   e) a first hollow prong having a fixed length, a distal end of said first hollow prong being open and sized to be received within a first nasal passageway and a proximal end of said first hollow prong being connected to said hollow body to provide fluid communication to said hollow body and to said pressure transducer;
   f) a second hollow prong having a fixed length, a distal end of said second hollow prong being open and sized to be received within a second nasal passageway and a proximal end of said second hollow prong being connected to said hollow body to provide fluid communication to said hollow body; and
   g) means to selectively inject said treatment gas into said hollow body or withdraw exhaled gases for analysis from said hollow body while simultaneously measuring pressure fluctuations in said hollow body.

2. The apparatus according to claim 1, wherein said first prong has a constantly tapering outer diameter which tapers from the proximal end of the tubular portion of said hollow body to distal end of said first prong, and said second prong has a constantly tapering outer diameter which tapers from the proximal end attached to the tubular portion of said hollow body to a distal end of said second prong.

3. The apparatus according to claim 1, wherein an oral prong is attached to said hollow body to provide fluid communication from the oral passageway to both ends of said hollow body whereby treatment gas may be simultaneously provided to both nasal passageways and the oral passageway, or gas withdrawn for analysis.

4. An apparatus for simultaneously measuring a patient's respiratory pressure and monitoring the composition of exhaled gases from the nostrils of a patient, the apparatus comprising:
- a) a gas receiving hollow body configured to be positioned at the upper lip of a patient and communicate with nasal passageways of a patient;
- b) a first conduit coupled to the hollow body;
- c) a second conduit coupled to the hollow body;
- d) a first hollow prong having a fixed length, a distal end of the first hollow prong being opened and sized to be received with a first nasal passage of the nose of a patient and a proximal end of the first hollow prong being connected to the hollow body to provide fluid communication to both the first conduit and the second conduit;
- e) a pressure transducer connected to, and in fluid communication with, the hollow body via one of the first or second conduits for measuring pressure fluctuations in the hollow body from gases exhaled from nasal passageways of a patient connected to the hollow body; and
- f) one of a carbon dioxide monitor or a treatment gas supply connected to, and in fluid communication with the hollow body via the other of the first or second conduit.

5. An apparatus for simultaneously measuring a patient's respiratory pressure and monitoring the composition of exhaled gases from the nostrils of a patient, the apparatus comprising:
- a) a gas receiving hollow body configured to be positioned at the upper lip of a patient and communicate with nasal passageways of a patient;
- b) a treatment gas supply connected to the hollow body via a first conduit to provide a supply of treatment gas to the interior of the hollow body;
- c) a carbon dioxide monitor connected to the hollow body via a second conduit, for aspirating and receiving gases exhaled from the nostrils of a patient; and
- d) a first hollow prong having a fixed length, a distal end of the first hollow prong being opened and sized to be received with a first nasal passage of the nose of a patient and a proximal end of the first hollow prong being connected to the hollow body to provide fluid communication to both ends of the hollow body.

* * * * *